US011173322B2

(12) United States Patent
Kuusela et al.

(10) Patent No.: US 11,173,322 B2
(45) Date of Patent: Nov. 16, 2021

(54) SYSTEMS AND METHODS FOR TREATMENT PLANNING USING CONTINUOUS QUALITY METRICS

(71) Applicant: Varian Medical Systems International AG, Cham (CH)

(72) Inventors: Esa Kuusela, Helsinki (FI); Lauri Jaakonpoika Halko, Helsinki (FI); Jarkko Peltola, Tuusula (FI); Emmi Ruokokoski, Helsinki (FI)

(73) Assignee: Varian Medical Systems International AG

( * ) Notice: Subject to any disclaimer, the term of this patent is extended or adjusted under 35 U.S.C. 154(b) by 138 days.

(21) Appl. No.: 16/237,489

(22) Filed: Dec. 31, 2018

(65) Prior Publication Data
US 2020/0206532 A1 Jul. 2, 2020

(51) Int. Cl.
*A61N 5/10* (2006.01)

(52) U.S. Cl.
CPC .................. *A61N 5/1031* (2013.01)

(58) Field of Classification Search
CPC .................................................. A61N 5/1031
See application file for complete search history.

(56) References Cited

U.S. PATENT DOCUMENTS

| 6,888,919 | B2 | 5/2005 | Graf |
| 7,162,008 | B2* | 1/2007 | Earl ..................... A61N 5/1031 378/149 |
| 7,649,981 | B2 | 1/2010 | Seppi et al. |
| 2013/0083004 | A1* | 4/2013 | Nord ....................... G06T 19/00 345/419 |
| 2013/0187062 | A1* | 7/2013 | Nord ..................... A61N 5/1031 250/492.1 |
| 2013/0324783 | A1* | 12/2013 | Zankowski .......... A61N 5/1031 600/1 |
| 2017/0087383 | A1* | 3/2017 | Peltola ................. A61N 5/1031 |
| 2018/0111006 | A1* | 4/2018 | Luan ....................... A61N 5/10 |
| 2018/0185669 | A1 | 7/2018 | Kuusela et al. |
| 2018/0193665 | A1* | 7/2018 | Kuusela ............... A61N 5/1031 |

(Continued)

FOREIGN PATENT DOCUMENTS

| EP | 3418926 A1 | 12/2018 | |
| WO | WO-2016088075 A1 * | 6/2016 | ............. G16H 20/40 |
| WO | WO 2018122251 A1 | 7/2018 | |

OTHER PUBLICATIONS

European Search Report dated May 26, 2020 for corresponding EP Patent Application No. 19219614.5.

(Continued)

*Primary Examiner* — Christine S. Kim
(74) *Attorney, Agent, or Firm* — Vista IP Law Group, LLP

(57) ABSTRACT

A treatment planning apparatus include: a quality metric generator configured to electronically generate a first quality metric based on input received via a user interface; an optimizer configured to determine treatment parameters for a treatment plan that is executable by a processing unit of a treatment machine to operate the treatment machine, wherein the optimizer is configured to determine the treatment parameters for the treatment plan based on the first quality metric; and a controller configured to influence how the optimizer performs optimization, wherein the controller is configured to provide a first continuous function for the first quality metric.

21 Claims, 6 Drawing Sheets

(56) References Cited

U.S. PATENT DOCUMENTS

2020/0206533 A1* 7/2020 Laaksonen ........... A61N 5/1031
2021/0158929 A1* 5/2021 Sjolund ................. G06N 3/08

OTHER PUBLICATIONS

Unkelbach, J et al.: "Optimization approaches to volumetric modulated arc therapy planning", Medical Physics, vol. 42, No. 3, Feb. 25, 2015 (Feb. 25, 2015), pp. 1367-1377, XP055214578, ISSN: 0094-2405, DOI: 10.1118/1.4908224.

* cited by examiner

Priority 0 goals:

1. Spine max dose ($q_1$) less than 45 Gy ($r_{11}$)
2. Target coverage ($-q_2$) better than 95% ($-r_{22}$)

Priority 1 goals:

3. Target coverage ($-q_2$) better than 98% ($-r_{23}$)
4. Mean Rectum dose ($q_3$) less than 35 Gy ($r_{34}$)

Priority 2 goals:

5. Mean Rectum dose ($q_3$) less than 30 Gy ($r_{35}$)

Residual goals:

Reduce Mean Rectum dose ($q_3$)

FIG. 3

SYSTEMS AND METHODS FOR TREATMENT PLANNING USING CONTINUOUS QUALITY METRICS

FIELD

This application relates generally to radiation therapy, and more specifically, to radiation treatment planning for radiation therapy.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Generally, a radiation treatment plan is determined before the radiation therapy is performed. During a radiation planning session, radiation treatment planning is performed before treatment radiation is delivered to a patient. This allows an accurate and precise dosage of radiation to be delivered to a patient. Embodiments of methods and systems for determining treatment plans are described herein.

SUMMARY

Optimization of Intensity modulated radiation therapy (e.g., IMRT, including both static gantry IMRT and VMAT) plan requires a definition of a cost function that is to be minimized. In some cases, the cost function may be defined so that it is to be maximized or minimized. Determining a cost function so that it takes into account various clinical goals in a balanced manner is difficult. The total cost function for a number of goals (j) and a number of metrics (i) may be defined as:

$$C(D)=\Sigma_j w_j \theta(q_i(D)-r_{ij})\{q_i(D)-r_{ij}\}^2$$

where the Heaviside step (or Unit step) function evaluates to zero when $r_{ij} > q(D)$. Here D is 3D dose matrix, $q_i$ is a quality metric, $r_{ij}$ is a goal value for that quality metric and $w_i$ is a scalar weight goal i.

The above formulation may not sufficiently take into account the relative importance of the goals or that it is beneficial to keep pushing the dose down even after the goal value is met. To achieve this behavior during treatment planning, a controller may be provided to control an optimization performed by a treatment planning optimizer. The controller may be configured to control the weights of the different goals based on what has been achieved. However, implementing such a treatment planning apparatus with such controller may be difficult.

One solution to address the above problem is 'lexicographic ordering' where a plan satisfying a prioritized list of clinical goals is searched by adding the most important non-satisfied goal into the cost function. This approach has, however, some drawbacks since the cost function may, in practice, require some tuning to keep higher level goals satisfied. The approach itself is quite strict and does not allow making trade-offs in situations where large improvement in lower priority goals (e.g., priority 2 goals) would be gained by accepting a slight worsening of one of the higher priority goals (e.g., priority 1 goal).

A new treatment planning apparatus and technique are described herein. A prioritized list of clinical goals is converted into continuous quality functions defining a utility function implicitly. The conversion from clinical goals to the continuous quality functions may be performed automatically by the treatment planning apparatus without user interaction. The continuous quality functions provide a way for guiding an optimization process performed by an optimizer of the treatment planning apparatus with more details than the clinical goals themselves. In some cases, the clinical goals may be treated by the treatment planning apparatus in a 'fuzzy' manner with no restrictive order. In some cases, the continuous quality functions may be optimized using a well-defined utility function. This allows robust optimization methods to be performed by the treatment planning apparatus. The new treatment planning apparatus and method described herein are advantageous because they allow systematically and intuitively handling cases where multiple goals share the same priority or where a user wants to guide which kind of trade-offs between different quality metrics are acceptable.

A treatment planning apparatus include: a quality metric generator configured to electronically generate a first quality metric based on input received via a user interface; an optimizer configured to determine treatment parameters for a treatment plan that is executable by a processing unit of a treatment machine to operate the treatment machine, wherein the optimizer is configured to determine the treatment parameters for the treatment plan based on the first quality metric; and a controller configured to influence how the optimizer performs optimization, wherein the controller is configured to provide a first continuous function for the first quality metric.

Optionally, the first continuous function is based on one or more prioritized clinical goals.

Optionally, the continuous function is configured to influence when a desired value of the first quality metric is to be achieved during the optimization performed by the optimizer.

Optionally, the continuous function is configured to influence how fast a first desired value of the first quality metric is to be achieved in the optimization performed by the optimizer relative to a second quality metric and/or relative to a second desired value of the first quality metric.

Optionally, the continuous function is configured to influence how the optimizer is to treat the first quality metric after its desired value has been achieved during the optimization.

Optionally, the first continuous function associates values of the first quality metric with respective prioritization metric values.

Optionally, the prioritization metric values comprise a first prioritization metric value, and wherein the first prioritization metric value is zero.

Optionally, the prioritization metric values comprise integers corresponding with respective prioritized goals.

Optionally, the prioritization metric values also comprise non-integers representing conditions before a prioritized goal is reached or after a prioritized goal has been reached.

Optionally, the prioritization metric values comprise a first integer corresponding with a first quality metric value of a first prioritized clinical goal, and a second integer corresponding with a second quality metric value of the first prioritized clinical goal.

Optionally, the first continuous function comprises an aberration function.

Optionally, the quality metric generator is also configured to electronically generate a second quality metric, and wherein the controller is configured to provide a second continuous function for the second quality metric.

Optionally, the controller is configured to influence, via both the first continuous function and the second continuous function, how the optimizer performs the optimization.

Optionally, the first continuous function has a first characteristic for a first range of prioritization metric values.

Optionally, the first continuous function has a second characteristic for a second range of prioritization metric values that is different from the first range of prioritization metric values.

Optionally, the first continuous function comprises a data structure associating values of the first quality metric with respective prioritization metric values.

Optionally, the apparatus is configured to determine an utility function P based on the first continuous function, wherein the optimizer is configured to perform the optimization based on the utility function.

Optionally, the optimizer is configured to: determine an initial solution S; calculate dose D based on the initial solution S; obtain the utility function P; calculate a gradient of the utility function P around D; and project the gradient of the utility function P into a solution space to obtain a gradient of S; determine a new solution S' based on the initial solution S, and the gradient of S.

Optionally, the first quality metric comprises a mean dose, a maximum dose, target coverage, or a relative or absolute volume of an organ having dose larger than a specified dose level.

A treatment planning method includes: electronically generating, by a quality metric generator, a first quality metric based on input received via a user interface; providing, by a controller, a first continuous function for the first quality metric; and determining, by an optimizer, treatment parameters for a treatment plan that is executable by a processing unit of a treatment machine to operate the treatment machine, wherein the treatment parameters for the treatment plan are determined based on the first quality metric; wherein the treatment parameters are determined based on an optimization performed by the optimizer, and wherein the optimization is influenced by the controller.

A product includes a non-transitory medium storing a set of instructions, an execution of which causes a treatment planning method to be performed, the treatment planning method comprising: electronically generating, by a quality metric generator, a first quality metric based on input received via a user interface; providing, by a controller, a first continuous function for the first quality metric; and determining, by an optimizer, treatment parameters for a treatment plan that is executable by a processing unit of a treatment machine to operate the treatment machine, wherein the treatment parameters for the treatment plan are determined based on the first quality metric; wherein the treatment parameters are determined based on an optimization performed by the optimizer, and wherein the optimization is influenced by the controller.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 3 illustrates examples of prioritized clinical goals;

DESCRIPTION OF THE EMBODIMENTS

Figure 1:
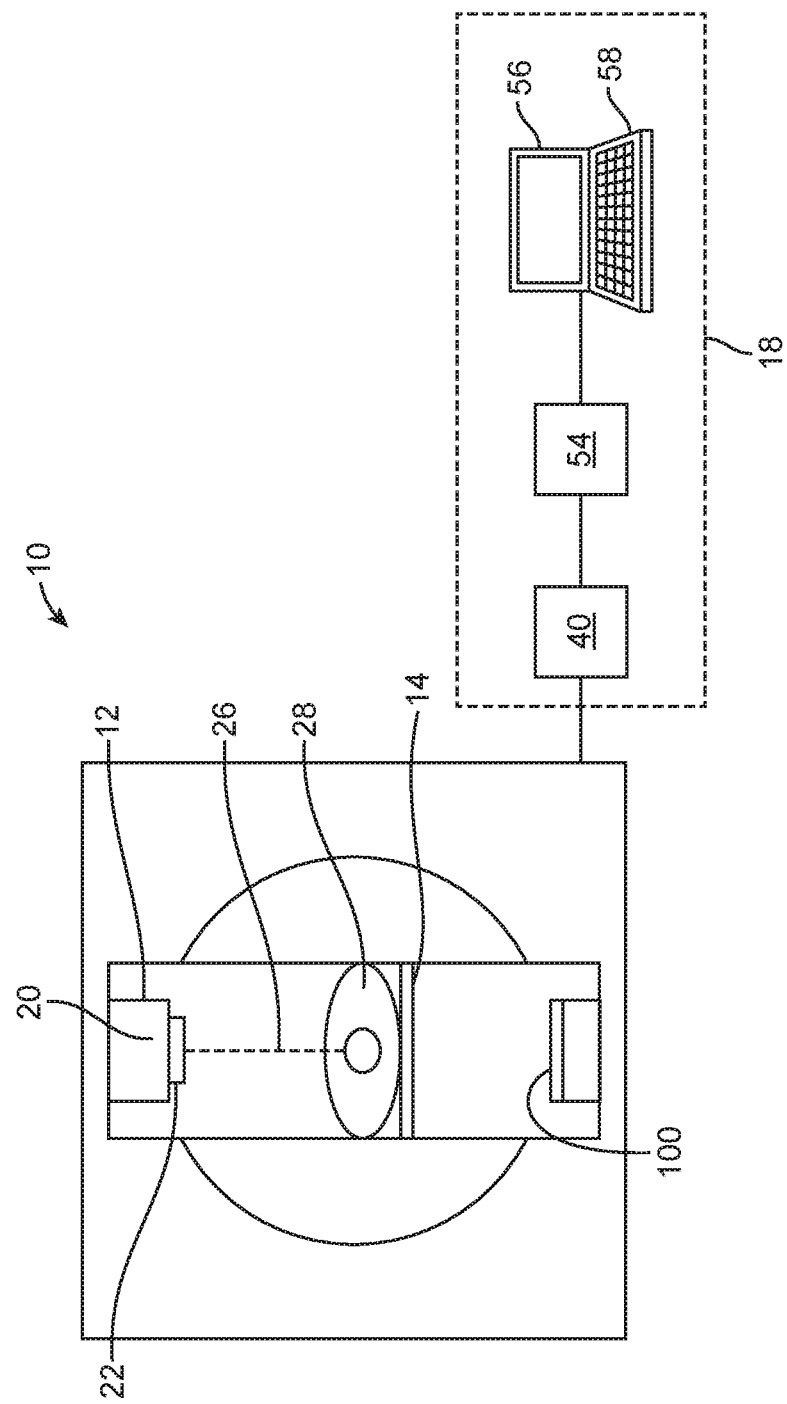
FIG. 1 illustrates a system for delivering radiation in accordance with a treatment plan determined in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. The system 10 includes a gantry 12 (in the form of an arm), a patient support 14 for supporting a patient, and a control system 18 for controlling an operation of the gantry 12. The system 10 also includes a radiation source 20 that projects a beam 26 of radiation towards a patient 28 while the patient 28 is supported on support 14, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager, such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. Pat. No. 6,888,919, entitled "RADIO-THERAPY APPARATUS EQUIPPED WITH AN ARTICULABLE GANTRY FOR POSITIONING AN IMAGING UNIT," issued on May 3, 2005, and U.S. Pat. No. 7,649,981, entitled "MULTI-ENERGY X-RAY SOURCE," issued on Jan. 19, 2010. In some embodiments, the radiation source 20 may be configured to emit high energy neutrons, electrons, protons, or other charged particles. In further embodiments, the radiation source 20 can be a diagnostic radiation source. In the illustrated embodiments, the radiation source 20 is coupled to the arm gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure. In such case, the gantry 12 may be fixed, and the patient support 14 is rotatable. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. Further, the radiation source 20 is not limited to delivering treatment energy in the form of x-ray, and may deliver other types of radiation energy. For example, in other embodiments, the radiation source 20 may be a proton source for delivering protons to treat patient, or other types of particle source for delivering other types of particles for treating a patient.

Figure 2:
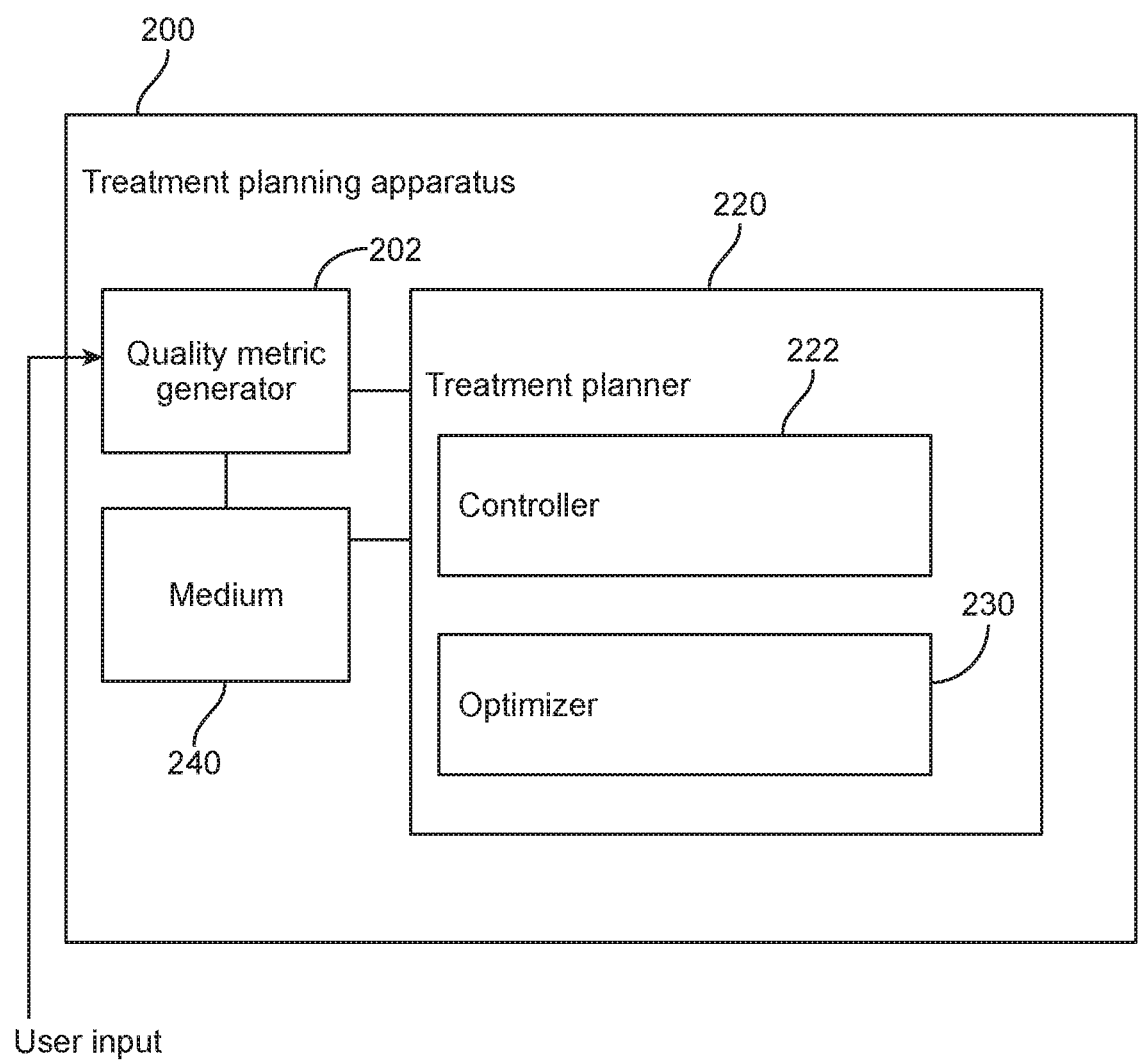
FIG. 2 illustrates an apparatus for determining a treatment plan in accordance with some embodiments.

FIG. 2 illustrates a treatment planning apparatus 200. The treatment planning apparatus 200 may be configured to provide a treatment plan for execution by a treatment machine, such as the one shown in FIG. 1. The treatment planning apparatus 200 includes a quality metric generator 202 configured to electronically generate a first quality metric based on input received via a user interface. The treatment planning apparatus 200 also includes a controller 222 and an optimizer 230. The controller 222 and the optimizer 230 may be considered to be parts of a treatment planner 220. The optimizer 230 is configured to determine treatment parameters for a treatment plan that is executable by a processing unit of a treatment machine (such as that shown in FIG. 1) to operate the treatment machine. The optimizer 230 is configured to determine the treatment parameters for the treatment plan based on the first quality metric. The controller 222 is configured to influence how the optimizer 230 performs optimization. In the illustrated embodiments, the controller 222 is configured to provide a first continuous function for the first quality metric, which serves to influence the manner in which the optimizer 230 performs optimization to determine the treatment parameters for the treatment plan.

By means of non-limiting examples, the first quality metric may be a mean dose, a maximum dose, target coverage, or a relative or absolute volume of an organ having dose larger than a specified dose level, etc.

In some embodiments, the first continuous function may be based on one or more prioritized clinical goals.

In general, a clinical goal may be represented as a quality metric (Q) and its associated goal value. Examples of clinical goals may be: spine max dose being less than 50 Gy, relative PTV volume getting less than prescription dose is less than 5%, mean dose of left parotid gland being less than 20 Gy, Volume of rectum having a maximum dose of 30 Gy is less than 3 cubic centimeters, max dose outside of target structures is less than 105% of the prescription dose, etc. Note that in the treatment planning apparatus 200, a same quality metric may appear in multiple different goals if associated to different goal values. Also, a treatment planning may involve multiple clinical goals represented as different respective quality metrics with corresponding goal value(s).

A goal set is called 'prioritized' if each goal in the goal set has a priority that describes how important it is compared to others. Note that in pure lexicographic ordering every goal has a unique priority or otherwise the optimization process will make random assumptions about the internal priority of those goals sharing the same priority. In one or more embodiments described herein, the concept of priority is attached to a plan quality. In some cases, the priority levels (prioritization metric values) may be named so that smaller priority value (smaller prioritization metric value) means that the priority is more important. Thus the number can be considered as an order of the priority. In the illustrated embodiments, the priority order 0 has a special meaning in that the plan will not be accepted for treatment if not all goals with priority 0 are not met. The internal ordering of goals within the group of 0 priority is thus not important. In other embodiments, the numbering of the priority levels (prioritization metric values) may be different from that described.

In some embodiments, a plan quality may be considered as being associated with the achieved goals. Accordingly, the prioritization metric values may be considered as plan quality values. For example, for a plan satisfying all the clinical goals up to priority n (and thus not satisfying at least one goal with priority n+1), the plan quality is close to a range [n, n+1]. The quality is near the lower bound if the goals with priority n are just barely met and it is near to the upper bound if the goal with priority n+1 is almost met. Thus, the plan quality is considered as being slightly larger than n+1, if the plan happens to satisfy a lot of goals with priority order larger than n+1.

FIG. 3 illustrates examples of prioritized clinical goal. As shown in FIG. 3, there are three quality metrics (i.e., spine max dose, target coverage, mean rectum dose) defining six goals. Note that one of the goals is a 'residual goal': it is the goal with lowest priority, and it does not have a goal value since it is merely prescribing that if multiple plans are satisfying all the goals from priority 0 to 2, the one with lowest rectum mean dose is going to be selected. In some embodiments, 'non-dosimetrical' parameters may be added to the goals. For example, the maximum allowed MU's may be prescribed as 2000 (defining new priority 0 goal), or that there is no point in pursuing the mean rectum dose below 35 Gy if it means using MU's more than 1500 (defining a new priority 1 goal), etc. Other examples of non-dosimetrical quality metrics may be 'treatment time', 'average leaf-pair-opening', etc.

In some embodiments, the plan quality may be deduced from individual quality metrics, by assigning a quality metric dependent plan quality. This means that one may define what would be the plan quality if only one of the quality metrics is evaluated. The total plan quality will then be a function of these individual quality metric dependent plan qualities. In some embodiments, the continuous functions $G_i$'s may be determined based on clinical knowledge. In some cases, the continuous functions may need to be defined only once for a certain kind of treatment. During treatment planning, the optimizer of the treatment planning apparatus will then find the optimal solution for a particular patient using the utility function derived from the continuous functions $G_i$'s.

In accordance with some embodiments, the treatment planning apparatus 200 provides a continuous way (continuous function) to define a plan quality. Such a plan quality may be used as a utility function in an optimization process. In such cases, an optimization algorithm may be utilized to maximize or minimize the utility function and get a treatment plan with highest possible quality. In some embodiments, the optimization algorithm may require calculation of the gradient of the utility function.

In some embodiments, the continuous function may be configured to influence when (i.e., temporally) a desired value of the first quality metric is to be achieved during the optimization performed by the optimizer 230. Alternatively or additionally, the continuous function may be configured to influence how fast a first desired value of the first quality metric is to be achieved in the optimization performed by the optimizer 230 relative to a second quality metric and/or relative to a second desired value of the first quality metric. Alternatively or additionally, the continuous function may be configured to influence how the optimizer 230 is to treat the first quality metric after its desired value has been achieved during the optimization.

Figure 4:
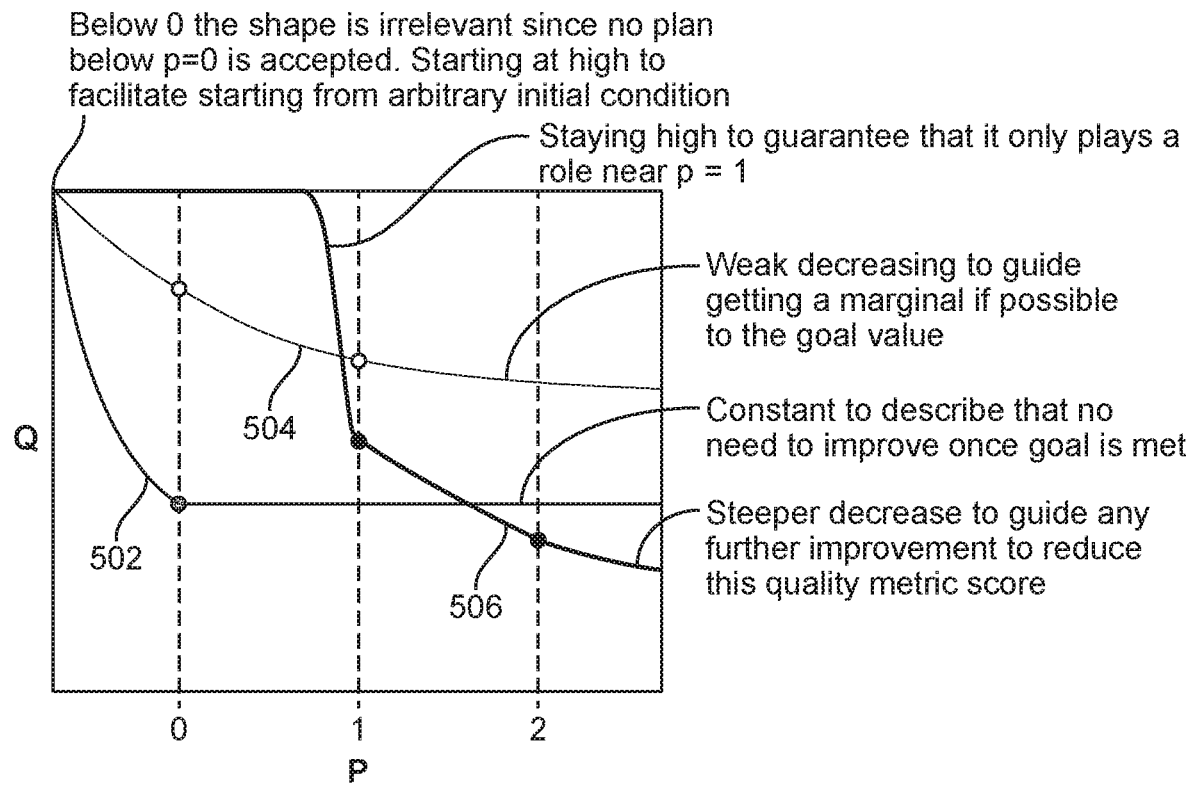
FIG. 4 illustrates examples of continuous functions associated with quality metrics of different clinical goals.

Turning back to the example of FIG. 3, since there are three quality metrics, there are also three functions defining three different plan qualities ($G_{spine\ max\ dose}$, $G_{target\ coverage}$, $G_{rectum\ mean\ dose}$). For clarity, the target coverage is defined in a way that a smaller numeric number is better (i.e. the relative volume in PTV having less than target dose). The continuous functions G may now be defined. First, it may be desirable to consider the continuous functions G for plan qualities below P=0 (below priority 0 goals). Note that while it may not matter how a plan is scored before the priority quality 0 is reached (since such a plan will not be accepted for treatment), it would still be desirable to guide the optimization process to search the solution space. In some embodiments, a continuous function G may begin with a corresponding plan quality value that is below zero (e.g., −1). Then the continuous function G is defined to be gradually increasing to 0 while the corresponding quality metric value is changing (e.g., decreasing) to the goal value of the goals in priority group 0. In other embodiments, instead of starting the quality metric value as some arbitrary defined high value, and letting the quality metric value decrease during the optimization to reach the goal value, the quality metric value may be arbitrary defined to start at a low value (e.g., 0), and the quality metric value may then increase during the optimization to reach the goal value. FIG. 4 illustrates a continuous function 502 for the quality metric "spine max dose" of FIG. 3, a continuous function 504 for the quality metric "target coverage" of FIG. 3, and a continuous function 506 for the quality metric "mean rectum dose" of FIG. 3.

In some embodiments, the treatment planning apparatus 200 may include a continuous function generator configured to generate the continuous function(s). In some cases, a user interface provided by the treatment planning apparatus 200 may allow a user to enter parameter(s) to define continuous functions for the different quality metrics. The entering of parameter(s) to define continuous function may be considered as an example of configuring the continuous function. Additionally or alternatively, the user interface may allow the user to select a desired continuous function from a list of previously formed continuous functions. The user may also use the user interface to modify the selected continuous functions for a particular patient. The modifying of the continuous function may be considered as another example of configuring the continuous function. In other embodiments, the continuous function generator may be configured to automatically generate continuous function for a certain user-defined quality metric (or clinical goal). For example, the continuous function generator may be configured to automatically convert a clinical goal to a continuous function. The continuous function will have more information that the clinical goal for influencing the manner in which the optimizer 230 performs treatment planning optimization.

As shown in FIG. 4, the rectum mean dose associated with the continuous function 506 ($G_{rectum\ mean\ dose}$) does not begin to reduce in value until after the priority level (or plan quality) 0 is reached. This is because the rectum mean dose is not involved in any priority level 0 goal (and is not considered to play a crucial role in the plan acceptance). Accordingly, the rectum mean dose starts to begin to reduce in value when P is a little less than 1, and continuous to reduce in value to reach 35 Gy when P reaches 1. The min value of $G_{rectum\ mean\ dose}$ may be selected based on how the clinician considers the clinical goal of 'rectum mean dose less than 35 Gy' is important relative to other clinical goals with priority 1 (e.g., clinical goal of 'PTV cold region less than 2%'). If both of the clinical goal can be satisfied, the plan quality would reach P=1. On the other hand, if both of the clinical goals are not satisfied, then it is the target coverage quality metrics (associated with continuous function 504) that is dictating the total plan quality. In particular, if the mean rectum dose starts reducing from a value when P is only slightly less than 1, it means that as long as the PTV cold region is significantly larger than 2% of the total PTV volume, it is the target coverage quality metrics that is dictating the total plan quality. Alternatively, the $G_{rectum\ mean\ dose}$ may be configured so that the rectum mean dose will start to reduce in value when P is almost reaching 0. This means that immediately once the plan is acceptable (plan quality has reached value 0), it is almost equally important to reduce both rectum mean dose and the PTV cold area volume.

Since 'spine max dose' is only involved to the clinical goal in priority group 0, $G_{Spine\ max\ dose}$ will shoot straight to infinity (i.e., P value will shoot through 1, 2, etc.) after reaching 45 Gy point (see curve 502 in FIG. 4, which represents the inverse of G, and has a flat slope after the prioritization metric value 0). This means this quality metric is not playing any further role in plan quality definition once the plan quality 0 has been achieved. Note that it is also possible to introduce a smoother behavior by letting the $G_{Spine\ max\ dose}$ increase quickly, but with finite slope, after the spine max dose is reduced below the 45 Gy goal value. The finite slope may reflect the clinical need to add some margin to the 45 Gy threshold, and it assumes that plan quality 1 corresponds with having a certain margin.

Similarly, $G_{target\ coverage}$ starts to increase (i.e., P value increasing) with increasing slope after the goal level associated to the goal in priority group 1 has been reached (see curve 504 in FIG. 4, which represents the inverse of G). This reflects the lesser and lesser clinical interest to keep paying attention to the further decrease of the cold area in PTV after the 2% goal level has been reached.

Finally it is notable that $G_{rectum\ mean\ dose}$ keeps increasing with reasonable slope even after the last goal level has been reached (see curve 506 in FIG. 4, which represents the inverse of G). This is indicating that the residual goal is dominating the optimization once all the defined goals have been reached.

As illustrated above, in some embodiments, the first continuous function may associate values of the first quality metric with respective prioritization metric values. For example, the first continuous function may comprise a data structure associating values of the first quality metric with respective prioritization metric values. In some cases, the first continuous function may have a first characteristic for a first range of prioritization metric values, and a second characteristic for a second range of prioritization metric values that is different from the first range of prioritization metric values.

Also as described herein, in some embodiments, the prioritization metric values may comprise integers corresponding with respective prioritized goals. For example, the prioritization metric value may be zero representing the highest priority goal, 1 representing the second highest priority goal, etc. Alternatively, the prioritization metric value may be 1 representing the highest priority goal, 2 representing the second highest priority goal, etc. Also, in some embodiments, the prioritization metric values may also comprise non-integers representing conditions before a prioritized goal is reached or after a prioritized goal has been reached.

Also as described herein, in some embodiments, the prioritization metric values may comprise a first integer corresponding with a first quality metric value of a first prioritized clinical goal, and a second integer corresponding with a second quality metric value of the first prioritized clinical goal.

Also as described herein, in some embodiments, the quality metric generator 202 is also configured to electronically generate a second quality metric. In such cases, the controller 222 is configured to provide a second continuous function for the second quality metric. Also, in some embodiments, the controller 222 may be configured to influence, via both the first continuous function and the second continuous function, how the optimizer 230 performs the optimization.

After individual continuous functions G's have been determined, they may be combined by the treatment planning apparatus 200 to form or define a total plan quality. The following are some examples of how a total plan quality may be defined.

1) Min-Quality-as-plan-quality: In some embodiments, the minimum quality may be utilized as the plan quality. In this implementation the total plan quality value is obtained by the minimum of all the individual G-functions. In other embodiments, instead of using a minimum function, the minimum function may be replaced with a soft-min function. In some cases, a soft-min may be defined by adding a minus sign to the exponent function argument of a soft-max function. Note that the introduction of the soft-min function introduces a new parameter describing how small differences in individual quality metrics are significant. This parameter has clinical meaning.

2) In other embodiments, the total plan quality may be defined as the one minimizing the difference to individual plan qualities calculated from the individual G's (or their inverse function). This implementation introduces a set of individual weights. The clinical meaning of those is that they provide a way to define clinically significant improvement beyond the goal value or clinically insignificant violation of the goal values.

3) In further embodiments, the total plan quality may be defined as the one minimizing the aberrations to different quality metric scorings. The aberration function is the generalization of the G continuous functions. The aberration indicates how large an error is made if plan with quality metric value q is called to have plan quality p'. Thus, the aberration is a function of both p and q. In some cases, for $p=G(q)$, the aberration function has value zero. For any larger p, the aberration may be positive (for example) to indicate that according to G the plan should be evaluated lower. For any smaller p, the aberration may be negative (for example). There are other ways to define the aberration. For example, the aberration may be defined as described above, and may be further multiplied by a constant. In some embodiments, the total plan quality may be evaluated by minimizing the total squared aberration.

There is freedom to define the aberration functions (thus allow many possibilities for describing clinical problems). However, for general solvability, it is beneficial that the aberration functions are monotonous both relative to p and to q. It is also possible to convert a single clinical goal systematically into a standard aberration function.

In some embodiments, to define the total plan quality, the user may also define a sensitivity (to be used in the aberration function definition) for each of the clinical quality metrics. For example, a sensitivity may be defined as $s^-_{rectum\ mean\ dose}=1$ Gy (which means that rectum mean dose need to improve 1 Gy beyond the goal value before it is considered clinically significant). As another example, a sensitivity may be defined as $s^+_{rectum\ mean\ dose}=0.1$ Gy (which means that rectum mean dose can be 0.1 Gy worse than the goal value before the goal violation is considered significant). These parameter pairs may be used as sensitivity parameters for the rectum mean dose. Similarly, parameter pairs may be defined to every quality metric. These allow the optimizer of the treatment planning apparatus to understand how to make compromises.

After the user has defined clinical goals to indicate the clinical desire for a particular planning task (such as low-risk prostate treatment), and after the continuous functions have been determined for the clinical goals, the optimizer of the treatment planning apparatus may then utilize such information to perform optimization in order to determine treatment parameters for a treatment plan.

It should be noted that in some cases, it does not matter if the utility function cannot be presented in explicit mathematical formula. This is because an implicit function may be used instead in some embodiments. The evaluation of the implicit function may be more complicated than evaluating an explicit function, but this is not computationally burdensome since the implicit utility function is a function of only a handful of quality metrics (each being explicit function). Accordingly, an evaluation of the implicit function may be achieved by solving a low-degree-of-freedom optimization problem during each optimization iteration by the optimizer 230. Furthermore for many implicit functions, it is possible to solve an explicit gradient around a given point, and it is thus possible to use such implicit utility function in gradient search optimization methods (such as steepest descent method, conjugate-gradient method, stochastic gradient method, etc.).

In some embodiments, the first continuous function may comprise an aberration function. In such cases, the optimizer 230 of the treatment planning apparatus 200 may implement an optimization algorithm using aberration function(s). For example, the aberration functions w may be defined by taking the G's defined above and combining sensitivity parameters to them. In one implementation, the aberration may be defined as:

$$W_i(p,q_i) = s_i^+(p - G_i(q_i)) \text{ if } p - G_i(q_i) > 0$$

$$s_i^-(G_i(q_i) - p) \text{ if } p - G_i(q_i) < 0$$

$$0 \text{ if } p - G_i(q_i) = 0$$

The utility function to be optimized is then $$P = \operatorname*{Arg\,min}_{p} \sum_i W_i^2(q_i(D), p)$$

The optimizer 230 of the treatment planning apparatus 200 may then solve the optimization problem based on the following algorithm:
1) Determine an initial solution S (can be a set of fluence maps, or leaf sequences, etc.)
2) Calculate dose D based on initial solution S
3) Define P related to the calculated dose D
4) Calculate gradient of P around the calculated dose D
5) Project the gradient of P into solution space S to get gradient of S
6) Find new solution S' based on the old solution S, and gradient of S
7) Repeat items 2-6 if convergence has not been reached by the optimizer 230.

Thus, as illustrated above, in some embodiments, the treatment planning apparatus 200 is configured to determine a utility function P based on the first continuous function. For example, the treatment planner 220 may utilize the first continuous function itself as the utility function P. Alternatively, the treatment planner 220 may determine the utility function P based on one or more features of the first continuous function. In some embodiments, the optimizer 230 is configured to perform the optimization based on the utility function.

In particular as illustrated above, in some embodiments, the optimizer 230 may be configured to: (1) determine an initial solution S; (2) calculate dose D based on the initial solution S; (3) obtain the utility function P; (4) calculate a gradient of the utility function P around D; and (5) project the gradient of the utility function P into a solution space to obtain a gradient of S; (6) determine a new solution S' based on the initial solution S, and the gradient of S. Also, in some embodiments, the optimizer 230 is configured to repeat the above items (2)-(6) until a solution converges. The solution results in one or more treatment parameters being determined for a treatment plan. The treatment plan may be stored in a non-transitory medium for later use. For example, the treatment plan may be retrieved later, and be executed by a treatment system (such as the system of FIG. 1) for operating the treatment system to deliver treatment radiation to treat the patient.

The above technique may be described mathematically. As discussed, FIG. 3 illustrates examples of prioritized clinical goals. In the examples, priority 0 goals are the highest priority goals, which describe features in the plan that must be met. Goals are in the form $q_i < r_{ij}$ where $q_i$ is a certain quality metric (e.g., it may be a function of dose D, machine parameters, etc.), and $r_{ij}$ is associated goal value (e.g., a scalar). Goals with priority 1 (priority 1 goals) are only evaluated once a solution is found satisfying all priority 0 goals. Similarly, goals with priority 2 (priority 2 goals) are only evaluated once a solution is found satisfying all priority 0 and priority 1 goals. Finally, a residual goal may be implemented to indicate how to continue optimization once all higher priority level goals are met.

In some cases, the weights $w_j$ for the priority goal classes may be chosen from a set that was manually determined to work the best. Additional heuristics may be manually input and/or determined for checking that the achieved goals remain achieved. Also, the order of the goals within a priority class may impact as to which goal gets more weight. Thus, such technique involves a complex manually tuned heuristic system.

In accordance with some embodiments, prioritized goals are first obtained. In some cases, the prioritized goals may be entered by a user via a user interface of a treatment planning apparatus. A prioritized goal may be represented by a quality metric with one or more values (goal values). Consider a set of quality metrics $\{q_i\}$. A quality metric may be 'Target coverage', 'Max dose in spinal cord', or 'mean dose of parotid gland' etc. Quality metrics may be functions of a dose matrix D, but is not necessary and optional for embodiments described herein. In some cases, quality metrics may be based on, for example, biological effect, delivery robustness, given MUs, etc. The notation below is assuming that $q_i$ is a function of D, but the dose matrix may be replaced by machine parameter(s). A clinical goal is a statement $q_i < r_{ij}$, where $r_{ij}$ is a goal value related to the clinical goal j. Each clinical goal is also associated to a priority $p_j$. Without loss of generality, $\{p_j\}$ may be natural numbers, with $p_j = 0$ having the special meaning that it describes acceptable plan. Note that more than one $p_j$ may have the same priority in some cases.

In accordance with some embodiments, all clinical goals related to quality metric $q_i$ may be combined into a single continuous, monotonically decreasing function $Q_i: R_+ \to R_+$ with inverse function $G_i: R_+ \to R_+$ where $R_+$ is the set of positive real numbers. The functions are defined so that for each clinical goal j having priority $p_i$ related to $q_i$ the following holds: $r_{ij} = Q_i(p_i)$. The continuous $G_i$'s can be understood as 'fuzzy' interpretation of whether goals with certain priority are met. For example, value $G_i$ (45 Gy)=1.0 means that quality score 45 Gy does not fulfill all aspects of quality metric $q_i$ related to level 2 priorities but the plan exceeds the quality described by goals $r_{ij}$ with priority level $p_j=1$ significantly. The relationship $g_i = G_i(q_i)$ maps the continuous quality metric value $q_i$ into continuous quality index $g_i$. Thus, the individual quality metrics are $q_i$'s and the function defining the plan quality based on a single quality metric is G.

A utility function may be defined as $p = P(\{g_i\})$, and the optimization problem is to find dose distribution (or machine control point sequence) that maximizes or minimizes the utility function. In some cases, the utility function may be presented also as p=P({G_i(q_i(D))})=P*(D), where P* is the utility function written as a function of the Dose matrix, which in turn could be presented as a function of fluence pixel values or machine parameters. The utility p is a scalar value that can be understood as a single number best describing the quality of an arbitrary plan. For example, if plan A has higher p value than plan B, it indicates that the plan A is considered to be better than plan B. Various techniques may be used to formulate a utility function that can best describe the clinical practice in evaluating treatment plans.

One possible choice of the utility function stems from considering that the plan quality is best described by the smallest individual quality factor:

$$P1(\{g_i\}) = \min_i \left(G_i(q_i(D))\right)$$

This utility function, although very simple, has a problem that its gradient with respect to D has only one component stemming from the smallest $G_i$. This means that the optimization will stop at the moment when the goal corresponding to the smallest quality factor is met. In practice this formulation is usually too restrictive, because it does not allow any trade-off considerations, i.e., a situation where a marginal decrease in some higher quality goal value is allowed in order to obtain a significant increase in some lower quality goal value.

In order to find a suitable utility function, it is not necessary to define P as an explicit function, but it is sufficient that P can be solved from a minimization problem P=Arg min$_p$ M (p, D) (i.e. finding p that minimize the given function M(p, D). Alternatively, P may be presented as a root-finding problem based on the equation B(p, D)=0. Note that differentiation of M(p, D) will lead to the formulation B(p, D)=0.

In some embodiments, the utility function may be implemented as follows:

$$M1(p, D) = \sum_i [w_i(Q_i(p) - q_i(D))]^2$$

where $w_i$ has a constant value when $Q_i(p)-q_i(D)>0$ (i.e. the given goal is not satisfied) and another smaller constant value when $Q_i(p)-q_i(D)<0$ (i.e. the given goal is satisfied) to ensure that non-satisfied goal is giving much larger contribution. The intuitive meaning of this function is to search a single value p that describes as well as possible the individual goals. The value p is considered to well describe individual goal j if the measured quality metric $q_j(D)$ does not differ significantly from the defined relation $q_j(p)$.

Note that variations to the described formula M1 may be easily created and implemented. For example, $w_i$ may be replaced by any function $W_i(Q_i(p)-q_i(D))$, and $Q_i(p)-q_i(D)$ may be replaced by a non-linear function. The exact shape of the function depends on clinical preferences of how the goals are actually interpreted. In some embodiments, p1 may be a suitable utility function if the priorities of different clinical goals are considered to be absolute (i.e. under no circumstances is lower-level goal considered before higher-level goals are met). In some embodiments, M1 may be a suitable utility function that is more 'opportunistic' in allowing breaking of higher-priority goals if significant improvements in other clinical goals are obtained as a trade-off.

In order to use the cost (utility) function as a part of an efficient optimization algorithm, it is beneficial if its gradient can be presented explicitly. Using implicit utility function as a part of gradient flow, the optimization method may be implemented as follows: For a solution candidate producing dose distribution D' the first step is to calculate $\{q_i(D')\}$ and solve p by minimizing M(p, D'). The optimization process may be converted into finding a root of dM/dp(p, D)=D', where dM1/dp is the implicit utility function derived partially by the p. This optimization task is not computationally demanding. Once p is known the gradient dp/dD may be calculated around D' by differentiating dM/dp(p,D) with respect to D, and solving dp/dD from that equation. In some cases, the gradient may be utilized to create a gradient of fluence matrices. The fluence matrices may be used in the next optimization iteration(s) to find the solution. For example, for function M1, the gradient $$dp/dD \sim \Sigma_i w_i dq_i/dD.$$

Note that the possibilities to generate $Q_i$'s (and additional parameters in M such as $w_i$) from clinical goals are numerous. As discussed, FIG. 4 illustrates examples of continuous functions $Q_i(p)$'s based on the prioritized clinical goals in FIG. 3. The goals are presented as dotted lines and the continuous curves representing the continuous functions are going through them. The continuation of the curves is in principle implemented smoothly but certain additional information may be used (see text in the figure). Note that the curves are continuous before p=0 to allow an acceptable plan to be reached starting from an initial condition not satisfying priority 0 objectives. The curves are also continuous after the p=2 to take into account residual goal, thereby allowing improvement of plan to be made by the treatment planning apparatus even further once all goals are met. The details of the curve specifications are just examples. Based on the examples of the continuous functions shown in FIG. 4, the following exemplary guidelines can be observed, which may allow getting good approximation directly from the set of prioritized goals:

(1) If after reaching certain goal level, any further improvement is irrelevant, and the $Q_i$ continues at flat line (see for example, function represented by line 502 in FIG. 4).

(2) If same quality metric $q_i$ has two goal levels with different priority, the $Q_i$ changes gradually from the higher priority goal value to the lower priority value (see for example, function represented by line 504 in FIG. 4).

(3) If certain quality metric $q_i$ has no priority goals higher than $p_j$, the curve is in maximum value until close to the priority $p_j$ (see for example, function represented by line 506 in FIG. 4).

As shown in FIG. 4, all $Q_i$'s are starting from maximum possible value $q_i$ that can be reached, but the shape of the curve has no clinical relevance before p=0, since any solution ending to p<0 is unacceptable. In other embodiments, one or more $Q_i$'s may start from a lowest possible values, or other arbitrary defined values.

In some embodiments, a more general solution of the form B(P, D) may be $$B1(p, D) = \sum_i W_i(q_i(D), p) = 0$$

where $W_i(q_i, p)$ is a function describing the signed 'deviation' between quality index and associated plan quality. For example, the following qualities may be specified $w_i$ for to map this more general approach to the continuous goal definition above.

(1) $W_i(q_i, p)$ vanishes as $q_i=Q_i(p)$: $W_i(Q_i(p), p)=0$, so with any given p and the associated $Q_i(p)$, the deviation vanishes.

(2) $W_q(q_i)=W_i(q_i, P_0)$ (with $p=P_0$) is a monotonically increasing function describing how deviations are handled. See FIGS. 5A-5C with explanation below.

(3) To avoid that B1 has multiple roots, it may be desirable to impose that $W_p(P)=W_i(q_{i0}, P)$ (with $q_i(D)=q_{i0}$) is monotonically decreasing function.

While B1 is quite general, it assumes that importance of reaching one goal does not depend upon whether the other goals would be satisfied. In some embodiments, another functional form may be provided in order to present such correlations.

Figures 5A, 5B, 5C:
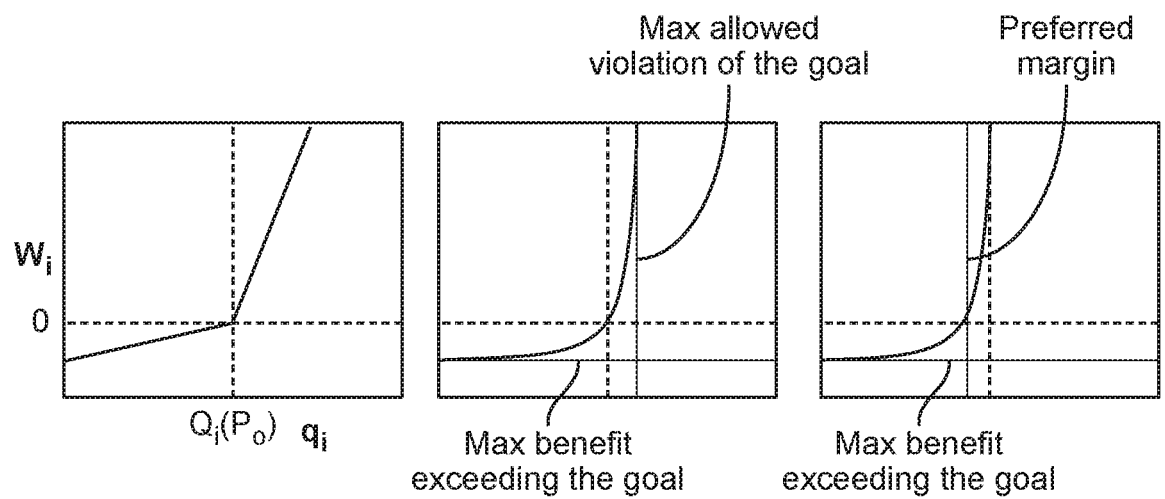
FIG. 5A-5C illustrate examples of relationships between quality index and associated plan quality.

FIGS. 5A-5C shows three different examples of $W_i(q, p)$ (with $p=P_0$). FIG. 5A describes a situation similar to that for function M1: a linear response is given but violation of the goal value is considered more severe than exceeding it. FIG. 5B describes a behavior where a specified maximum violation of the goal value is acceptable, and the benefit of exceeding the goal is saturated at some point. FIG. 5C describes a variation of FIG. 5B, where the curve is shifted so that a given goal is always satisfied.

In some embodiments, it may be useful for the user to get, as output of the optimization process, the individual $g_i$'s to see which features were contributing most to the final solution. The treatment planning apparatus described herein may be configured to provide such output. In some cases, if the utility function is formulated as the example $B_1(p, D)$, the individual $W_i(q_i(D), p)$ may be presented by the treatment planning apparatus.

Figure 6:
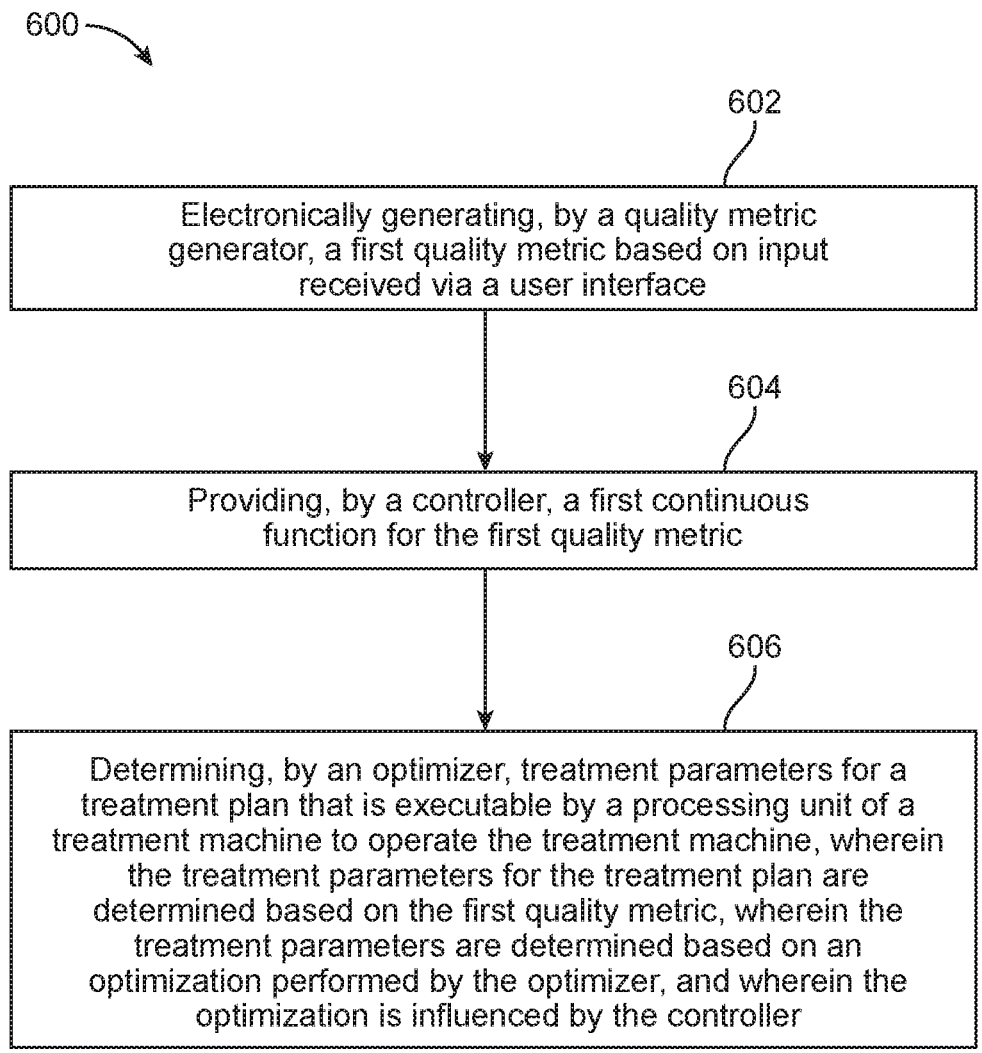
FIG. 6 illustrates a method for determining a treatment plan in accordance with some embodiments.
Figure 7:
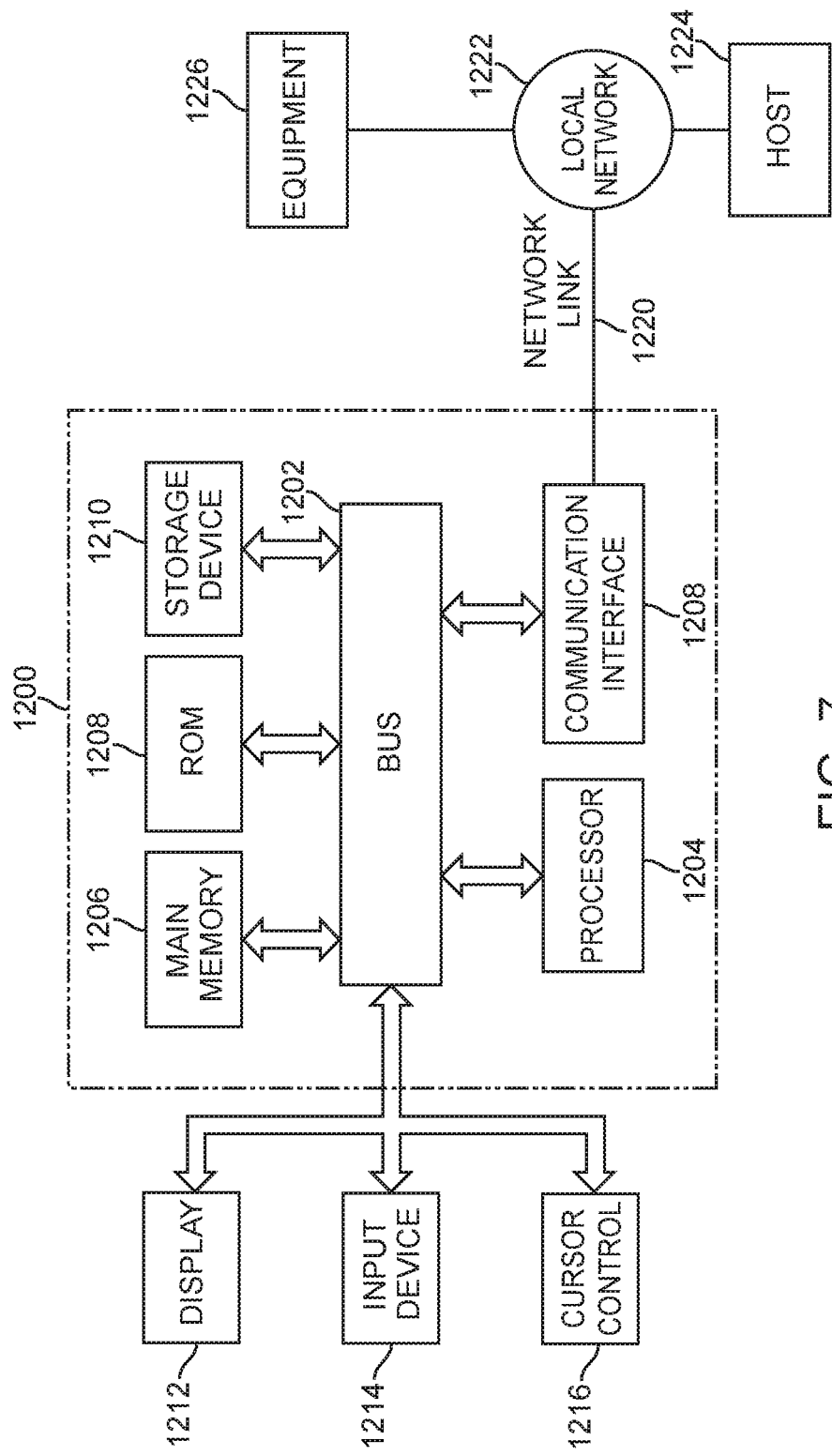
FIG. 7 is a block diagram of a treatment planning apparatus.

FIG. 6 illustrates a treatment planning method 600 in accordance with some embodiments. The treatment planning method 600 includes: electronically generating, by a quality metric generator, a first quality metric based on input received via a user interface (item 602); providing, by a controller, a first continuous function for the first quality metric (item 604); and determining, by an optimizer, treatment parameters for a treatment plan that is executable by a processing unit of a treatment machine to operate the treatment machine, wherein the treatment parameters for the treatment plan are determined based on the first quality metric, wherein the treatment parameters are determined based on an optimization performed by the optimizer, and wherein the optimization is influenced by the controller (item 606).

In some embodiments, a product may be provided for implementing one or more features described herein. The product may include a non-transitory medium storing a set of instructions, an execution of which causes a treatment planning method to be performed. For example, the treatment planning method may be the method 600 of FIG. 6. The treatment planning method may include: electronically generating, by a quality metric generator, a first quality metric based on input received via a user interface; providing, by a controller, a first continuous function for the first quality metric; and determining, by an optimizer, treatment parameters for a treatment plan that is executable by a processing unit of a treatment machine to operate the treatment machine, wherein the treatment parameters for the treatment plan are determined based on the first quality metric. In the illustrated embodiments, the treatment parameters are determined based on an optimization performed by the optimizer, wherein the optimization is influenced by the controller. In some embodiments, the set of instructions may include instructions for implementing the quality metric generator 202, and instructions for implementing the treatment planner 220. The instructions for implementing the treatment planner 220 may include instructions for implementing the controller 222, and instructions for implementing the optimizer 230.

As illustrated above, embodiments of the treatment planning apparatus 200 and the method 300 described herein provide technical improvements in treatment planning devices by making them more accurate in achieving clinical goals. The result is a treatment plan that correctly reflects the desired clinical goals, so that when the treatment plan is executed by a treatment machine, the desired clinical goals will be achieved. This has a practical and concrete impact in the real-world. Also, the controller 222 described herein is advantageous because it provides continuous function(s) is more detailed than just a quality metric of a clinical goal. The continuous function(s) influences the manner in which the treatment planner 220 performs optimization to determine treatment parameters of a treatment plan. Accordingly, the controller 222 and the continuous function(s) it provides can more accurately and desirably control the manner in which the optimizer 230 performs optimization for determining the treatment parameters.

Although the above embodiments have been described with reference to delivering treatment radiation that is in the form of x-rays, in other embodiments, the system and technique described herein may be used for other types of treatment energy. For examples, in other embodiments, in other embodiments, the radiation source 20 may be a proton source for delivering protons to treat a patient, or an electron source for delivering electrons. Accordingly, embodiments of the treatment planning technique described herein may be used to determine treatment plan for other types of treatment, such as proton treatment.

It should be noted that the term "continuous function", as used in this specification, does not necessarily require the function to be continuous for all ranges of values. A continuous function may be continuous for any range(s) of values or for all ranges of values.

Also, the terms "utility function" and "cost function" may be interchanged, and as used in this specification, may refer to any function to be maximized or minimized by an optimizer during treatment planning optimization.

Treatment Planning Apparatus

FIG. 9 is a block diagram that illustrates an embodiment of a treatment planning apparatus 1200. The treatment planning apparatus 1200 may be the treatment planning apparatus 200 of FIG. 2. As shown in FIG. 9, the treatment planning apparatus 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. The treatment planning apparatus 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The treatment planning apparatus 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The treatment planning apparatus 1200 may be coupled via the bus 1202 to a display 1212, such as a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The treatment planning apparatus 1200 may be used for performing various functions (e.g., calculation) in accordance with the embodiments described herein. According to one embodiment, such use is provided by treatment planning apparatus 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process acts described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Volatile media includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the treatment planning apparatus 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The treatment planning apparatus 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the treatment planning apparatus 1200, are exemplary forms of carrier waves transporting the information. The treatment planning apparatus 1200 can send messages and receive data, including program code, through the network(s), the network link 1220, and the communication interface 1218.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. A treatment planning apparatus, comprising:
   a quality metric generator configured to electronically generate a first quality metric based on input received via a user interface;
   an optimizer configured to electronically determine treatment parameters for a treatment plan that is executable by a processing unit of a treatment machine to operate the treatment machine, wherein the optimizer is configured to determine the treatment parameters for the treatment plan based on the first quality metric; and
   a controller, implemented at least partly using hardware, configured to electronically communicate with the optimizer to influence how the optimizer electronically performs optimization, wherein the controller is configured to provide a first continuous function for the first quality metric, wherein the treatment planning apparatus is configured to use the first continuous function during the optimization to influence how the optimizer performs the optimization, wherein the first continuous function indicates how fast a first desired value of the first quality metric is to be achieved in the optimization in relation to multiple different priority levels, wherein the treatment planning apparatus is configured to influence how the optimizer electronically performs the optimization by controlling the optimizer based on the first continuous function indicating how fast the first desired value of the first quality metric is to be achieved in the optimization in relation to the multiple different priority levels, thereby improving a performance of the treatment planning apparatus, and wherein the optimizer as influenced by the controller based on the first continuous function is configured to determine one or more of the treatment parameters for the treatment plan.

2. The apparatus of claim 1, wherein the first continuous function is based on one or more prioritized clinical goals.

3. The apparatus of claim 1, wherein the first continuous function is configured to influence when a desired value of the first quality metric is to be achieved during the optimization performed by the optimizer.

4. The apparatus of claim 1, wherein the first continuous function is configured to influence how fast the first desired value of the first quality metric is to be achieved in the optimization performed by the optimizer relative to a second quality metric and/or relative to a second desired value of the first quality metric.

5. The apparatus of claim 1, wherein the first continuous function is configured to influence how the optimizer is to treat the first quality metric when performing additional optimization task(s) during the optimization after first desired value of the first quality metric has been achieved during the optimization.

6. The apparatus of claim 1, wherein the first continuous function associates values of the first quality metric with respective prioritization metric values.

7. The apparatus of claim 6, wherein the prioritization metric values comprise a first prioritization metric value, and wherein the first prioritization metric value is zero.

8. The apparatus of claim 6, wherein the prioritization metric values comprise integers corresponding with respective prioritized goals.

9. The apparatus of claim 8, wherein the prioritization metric values also comprise non-integers representing conditions before a prioritized goal is reached or after a prioritized goal has been reached.

10. The apparatus of claim 6, wherein the prioritization metric values comprise a first integer corresponding with a first quality metric value of a first prioritized clinical goal, and a second integer corresponding with a second quality metric value of the first prioritized clinical goal.

11. The apparatus of claim 1, wherein the first continuous function comprises an aberration function.

12. The apparatus of claim 1, wherein the quality metric generator is also configured to electronically generate a second quality metric, and wherein the controller is configured to provide a second continuous function for the second quality metric.

13. The apparatus of claim 12, wherein the controller is configured to influence, via both the first continuous function and the second continuous function, how the optimizer performs the optimization.

14. The apparatus of claim 1, wherein the first continuous function has a first characteristic for a first range of prioritization metric values.

15. The apparatus of claim 14, wherein the first continuous function has a second characteristic for a second range of prioritization metric values that is different from the first range of prioritization metric values.

16. The apparatus of claim 1, wherein the first continuous function comprises a data structure associating values of the first quality metric with respective prioritization metric values.

17. The apparatus of claim 1, wherein the apparatus is configured to determine a utility function P based on the first continuous function, wherein the optimizer is configured to perform the optimization based on the utility function.

18. A treatment planning apparatus, comprising:
a quality metric generator configured to electronically generate a first quality metric based on input received via a user interface;
an optimizer configured to electronically determine treatment parameters for a treatment plan that is executable by a processing unit of a treatment machine to operate the treatment machine, wherein the optimizer is configured to determine the treatment parameters for the treatment plan based on the first quality metric; and
a controller, implemented at least partly using hardware, configured to electronically communicate with the optimizer to influence how the optimizer electronically performs optimization, wherein the controller is configured to provide a first continuous function for the first quality metric;
wherein the optimizer is configured to:
determine an initial solution S;
calculate a dose D based on the initial solution S;
obtain an utility function P;
calculate a gradient of the utility function P around D; and
project the gradient of the utility function P into a solution space to obtain a gradient of S;
determine a new solution S' based on the initial solution S, and the gradient of S, wherein the determined new solution S' comprises one or more of the treatment parameters for the treatment plan that have been optimized by the optimizer as influenced by the controller based on the first continuous function.

19. The apparatus of claim 1, wherein the first quality metric comprises a mean dose, a maximum dose, a target coverage, or a relative or an absolute volume of an organ having a dose larger than a specified dose level.

20. A treatment planning method performed by a treatment planning apparatus, the method comprising:
electronically generating, by a quality metric generator, a first quality metric based on input received via a user interface;
providing, by a controller, a first continuous function for the first quality metric, wherein the controller is implemented at least partly using hardware, and is configured to electronically communicate with an optimizer; and
electronically determining, by the optimizer, treatment parameters for a treatment plan that is executable by a processing unit of a treatment machine to operate the treatment machine, wherein the treatment parameters for the treatment plan are determined based on the first quality metric;
wherein the treatment parameters are determined based on an optimization electronically performed by the optimizer, and wherein the first continuous function is used by the treatment planning apparatus during the optimization to influence how the optimizer performs the optimization, wherein the first continuous function indicates how fast a first desired value of the first quality metric is to be achieved in the optimization in relation to multiple different priority levels, wherein how the optimizer electronically performs the optimization is influenced by controlling the optimizer based on the first continuous function indicating how fast the first desired value of the first quality metric is to be achieved in the optimization in relation to the multiple different priority levels, and wherein the optimizer as influenced by the controller based on the first continuous function is configured to determine one or more of the treatment parameters for the treatment plan.

21. A product having a non-transitory medium storing a set of instructions, an execution of which causes a treatment planning method to be performed by a treatment planning apparatus, the treatment planning method comprising:

electronically generating, by a quality metric generator, a first quality metric based on input received via a user interface;

providing, by a controller, a first continuous function for the first quality metric, wherein the controller is implemented at least partly using hardware, and is configured to electronically communicate with an optimizer; and electronically determining, by the optimizer, treatment parameters for a treatment plan that is executable by a processing unit of a treatment machine to operate the treatment machine, wherein the treatment parameters for the treatment plan are determined based on the first quality metric;

wherein the treatment parameters are determined based on an optimization electronically performed by the optimizer, and wherein the first continuous function is used by the treatment planning apparatus during the optimization to influence how the optimizer performs the optimization, wherein the first continuous function indicates how fast a first desired value of the first quality metric is to be achieved in the optimization in relation to multiple different priority levels, wherein how the optimizer electronically performs the optimization is influenced by controlling the optimizer based on the first continuous function indicating how fast the first desired value of the first quality metric is to be achieved in the optimization in relation to the multiple different priority levels, and wherein the optimizer as influenced by the controller based on the first continuous function is configured to determine one or more of the treatment parameters for the treatment plan.

\* \* \* \* \*